(12) United States Patent
Kosugou

(10) Patent No.: US 10,148,896 B2
(45) Date of Patent: Dec. 4, 2018

(54) HEART RATE DETECTION DEVICE AND FACIAL RECOGNITION SYSTEM WITH THE HEART RATE DETECTION DEVICE

(71) Applicant: Kabushiki Kaisha Toshiba, Minato-ku (JP)

(72) Inventor: Eiichirou Kosugou, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 14/926,412

(22) Filed: Oct. 29, 2015

(65) Prior Publication Data

US 2016/0191822 A1    Jun. 30, 2016

(30) Foreign Application Priority Data

Dec. 26, 2014  (JP) ................... 2014-265998

(51) Int. Cl.
| | |
|---|---|
| *H04N 5/33* | (2006.01) |
| *G06K 9/20* | (2006.01) |
| *H04N 9/04* | (2006.01) |
| *A61B 5/024* | (2006.01) |
| *A61B 5/1171* | (2016.01) |

(Continued)

(52) U.S. Cl.
CPC ........... *H04N 5/33* (2013.01); *A61B 5/02433* (2013.01); *A61B 5/1176* (2013.01); *G06K 9/00255* (2013.01); *G06K 9/209* (2013.01); *G06K 9/2018* (2013.01); *H01L 27/1464* (2013.01); *H01L 27/14621* (2013.01); *H04N 5/23219* (2013.01);

(Continued)

(58) Field of Classification Search
None
See application file for complete search history.

(56) References Cited

U.S. PATENT DOCUMENTS

| | | | | |
|---|---|---|---|---|
| 2006/0157806 | A1* | 7/2006 | Rhodes | H01L 27/14609 257/414 |
| 2011/0181752 | A1* | 7/2011 | Nakashima | H04N 9/045 348/223.1 |

(Continued)

FOREIGN PATENT DOCUMENTS

| | | | |
|---|---|---|---|
| JP | 09262213 | A * | 10/1997 |
| JP | 2008-235753 | | 10/2008 |

(Continued)

*Primary Examiner* — Sumati Lefkowitz
*Assistant Examiner* — Jiangeng Sun
(74) *Attorney, Agent, or Firm* — Oblon, McClelland, Maier & Neustadt, L.L.P.

(57) ABSTRACT

According to an embodiment, a facial recognition system includes an image sensor, a facial recognition processing unit, a heart rate detection unit, and an authentication unit. The image sensor detects incident light by an infrared pixel, and outputs detected infrared information. The facial recognition processing unit recognizes the face of a person based on image information signal captured by the image sensor. The heart rate detection unit reads the heart rate of the person from pulses in a blood vessel in the face based on the infrared information. The authentication unit receives facial recognition signal outputted from the facial recognition processing unit. The authentication unit authenticates the person as an identical person when the heart rate is inputted, and authenticates the person as a photograph when the heart rate is not inputted.

8 Claims, 10 Drawing Sheets

(51) Int. Cl.
*G06K 9/00* (2006.01)
*H04N 5/232* (2006.01)
*H01L 27/146* (2006.01)

(52) U.S. Cl.
CPC ......... *H04N 5/23245* (2013.01); *H04N 9/045* (2013.01); *G06K 2009/00939* (2013.01)

(56) References Cited

U.S. PATENT DOCUMENTS

2013/0334402 A1   12/2013  Izuha et al.
2015/0186711 A1*  7/2015  Baldwin ............ G06K 9/00228
                                            382/118

FOREIGN PATENT DOCUMENTS

| JP | 2012-146920 | 8/2012 |
| JP | 2014-17468 | 1/2014 |
| JP | 2014-71628 | 4/2014 |

* cited by examiner

| CFb/ | Cfir/ |
| B PIXEL | IR PIXEL |
| CFg/ | CFr/ |
| G PIXEL | R PIXEL |

FIG. 4

| CFb/<br>B PIXEL | CFg/<br>G PIXEL | CFb/<br>B PIXEL | CFir/<br>IR PIXEL |
|---|---|---|---|
| CFg/<br>G PIXEL | CFr/<br>R PIXEL | CFg/<br>G PIXEL | CFr/<br>R PIXEL |
| CFb/<br>B PIXEL | CFg/<br>G PIXEL | CFb/<br>B PIXEL | CFg/<br>G PIXEL |
| CFg/<br>G PIXEL | CFr/<br>R PIXEL | CFg/<br>G PIXEL | CFr/<br>R PIXEL |

FIG. 5A

| CFb/B<br>PIXEL | CFg/G<br>PIXEL | CFb/B<br>PIXEL | CFg/G<br>PIXEL | CFb/B<br>PIXEL | CFg/G<br>PIXEL | CFb/B<br>PIXEL | CFir/IR<br>PIXEL |
|---|---|---|---|---|---|---|---|
| CFg/G<br>PIXEL | CFr/R<br>PIXEL | CFg/G<br>PIXEL | CFr/R<br>PIXEL | CFg/G<br>PIXEL | CFr/R<br>PIXEL | CFg/G<br>PIXEL | CFr/R<br>PIXEL |
| CFb/B<br>PIXEL | CFg/G<br>PIXEL | CFb/B<br>PIXEL | CFg/G<br>PIXEL | CFb/B<br>PIXEL | CFg/G<br>PIXEL | CFb/B<br>PIXEL | CFg/G<br>PIXEL |
| CFg/G<br>PIXEL | CFr/R<br>PIXEL | CFg/G<br>PIXEL | CFr/R<br>PIXEL | CFg/G<br>PIXEL | CFr/R<br>PIXEL | CFg/G<br>PIXEL | CFr/R<br>PIXEL |
| CFb/B<br>PIXEL | CFg/G<br>PIXEL | CFb/B<br>PIXEL | CFg/G<br>PIXEL | CFb/B<br>PIXEL | CFg/G<br>PIXEL | CFb/B<br>PIXEL | CFg/G<br>PIXEL |
| CFg/G<br>PIXEL | CFr/R<br>PIXEL | CFg/G<br>PIXEL | CFr/R<br>PIXEL | CFg/G<br>PIXEL | CFr/R<br>PIXEL | CFg/G<br>PIXEL | CFr/R<br>PIXEL |
| CFb/B<br>PIXEL | CFg/G<br>PIXEL | CFb/B<br>PIXEL | CFg/G<br>PIXEL | CFb/B<br>PIXEL | CFg/G<br>PIXEL | CFb/B<br>PIXEL | CFg/G<br>PIXEL |
| CFg/G<br>PIXEL | CFr/R<br>PIXEL | CFg/G<br>PIXEL | CFr/R<br>PIXEL | CFg/G<br>PIXEL | CFr/R<br>PIXEL | CFg/G<br>PIXEL | CFr/R<br>PIXEL |

FIG. 5B tion coefficient of each material versus wavelength (energy);

HEART RATE DETECTION DEVICE AND FACIAL RECOGNITION SYSTEM WITH THE HEART RATE DETECTION DEVICE

CROSS REFERENCE TO RELATED APPLICATION

This application is based upon and claims the benefit of priority from the prior Japanese Patent Application No. 2014-265998, filed on Dec. 26, 2014, the entire contents of which are incorporated herein by reference.

FIELD

Embodiments described herein relate to a heart rate detection device and a facial recognition system with the heart rate detection device.

BACKGROUND

Face authentication requires an ability to discriminate between an identical person and a photograph. It is impossible to discriminate between the identical person and the photograph by color or image processing. The face authentication using a video signal in a visible light region has problems of a low sensitivity, a long time required to complete face authentication, and a low accuracy.

Hence, there is a demand for a facial recognition system capable of executing face authentication with a high accuracy.

BRIEF DESCRIPTION OF THE DRAWINGS

FIG. 4 is a schematic plan view illustrating a pixel array according to the first embodiment;

FIG. 5 includes schematic plan views each illustrating a modification of the pixel array in which an IR pixel is arranged at 1/16 in FIG. 5A and at 1/64 in FIG. 5B;

DETAILED DESCRIPTION

Figure 1:
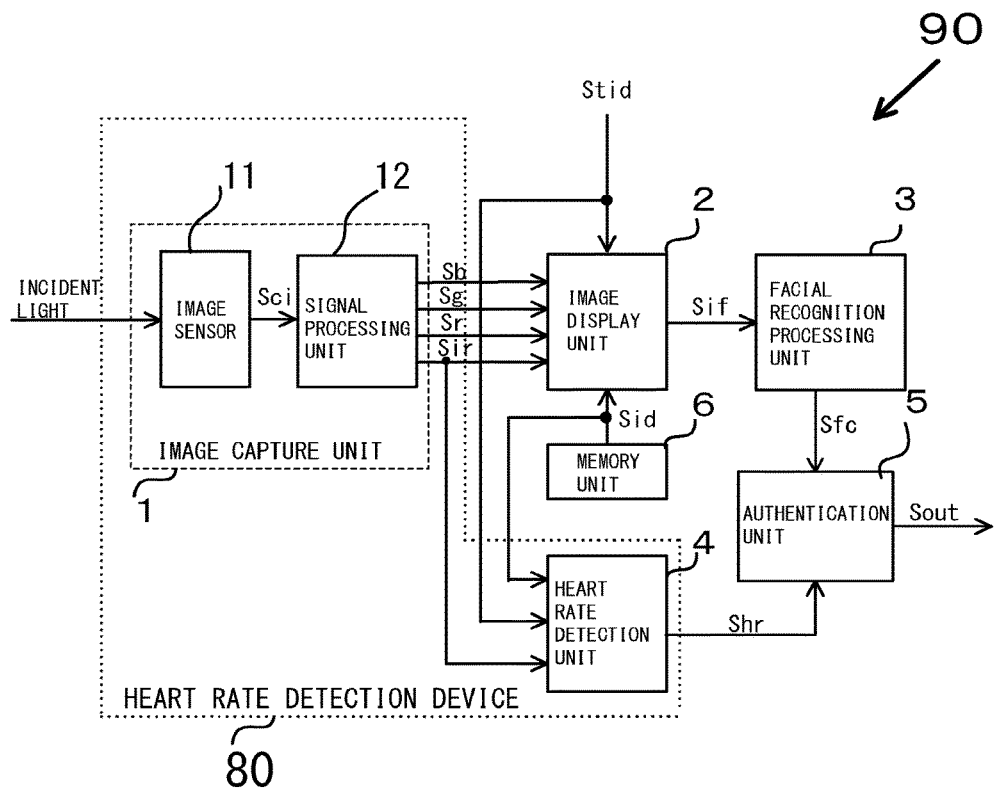
FIG. 1 is a block diagram illustrating a facial recognition system according to a first embodiment.

According to an embodiment, a facial recognition system includes an image sensor, a facial recognition processing unit, a heart rate detection unit, and an authentication unit. The image sensor detects incident light by an infrared pixel, and outputs detected infrared information. The facial recognition processing unit recognizes the face of a person based on image information signal captured by the image sensor. The heart rate detection unit reads the heart rate of the person from pulses in a blood vessel in the face based on the infrared information. The authentication unit receives facial recognition signal outputted from the facial recognition processing unit. The authentication unit authenticates the person as an identical person when the heart rate is inputted, and authenticates the person as a photograph when the heart rate is not inputted.

Hereinafter, further embodiments will be described with reference to the drawings. In the drawings, the same reference numeral indicates the same or similar portions.

Figure 2:
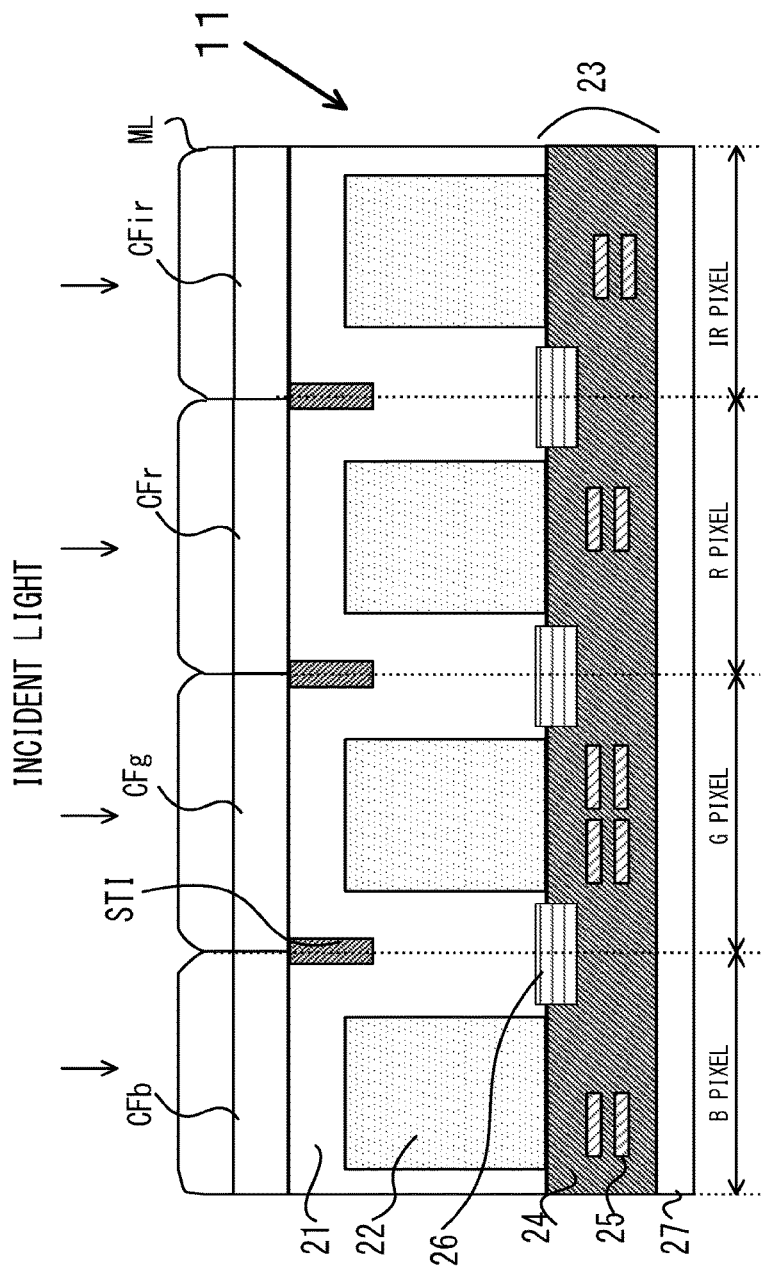
FIG. 2 is a cross sectional view of an image sensor according to the first embodiment.

A heart rate detection device and a facial recognition system with the heart rate detection device according to a first embodiment will be described with reference to the drawings. FIG. 1 is a block diagram illustrating the facial recognition system. FIG. 2 is a cross sectional view of an image sensor. In the first embodiment, the image sensor is provided with an IR pixel and an infrared band-pass color filter. This enables heart rate detection to be performed with a high sensitivity, and thus face authentication to be highly-accurately executed depending on the presence or absence of the heart rate.

As illustrated in FIG. 1, a facial recognition system 90 includes an image display unit 2, a facial recognition processing unit 3, an authentication unit 5, a memory unit 6, and a heart rate detection device 80. The facial recognition system 90 is capable of discriminating between an identical person and a photograph with a high accuracy.

The heart rate detection device 80 includes an image capture unit 1 and a heart rate detection unit 4. The image capture unit 1 includes an image sensor 11 and a signal processing unit 12. The heart rate detection device 80 detects the heart rate of a person with a high sensitivity from pulses in a blood vessel by using infrared information detected by an infrared pixel. The heart rate detection device 80 and the facial recognition system 90 are equipped in a handheld terminal or the like.

The image sensor 11 receives incident light, and outputs an image signal obtained by photoelectric conversion of the incident light.

As illustrated in FIG. 2, the image sensor 11 includes a B pixel (blue pixel), a G pixel (green pixel), an R pixel (red pixel), and an IR pixel (infrared pixel).

In the image sensor 11, a support substrate 27, a wiring layer 23, photodiodes each including a semiconductor layer 21 and a semiconductor layer 22, color filters, and micro lenses ML are stacked. The image sensor 11 is a back-illuminated sensor to which incident light is inputted through the micro lenses ML. The semiconductor layer 21 is a P-type semiconductor layer, for example. The semiconductor layer 22 is an N-type semiconductor layer.

In a B pixel area, a photodiode (first photodiode) including the semiconductor layer 21 and the semiconductor layer 22, a color filter CFb, and the micro lens ML are stacked. In a G pixel area, a photodiode (second photodiode) including the semiconductor layer 21 and the semiconductor layer 22, a color filter CFg, and the micro lens ML are stacked. In an R pixel area, a photodiode (third photodiode) including the semiconductor layer 21 and the semiconductor layer 22, a color filter CFr, and the micro lens ML are stacked. In an IR pixel area, a photodiode (fourth photodiode) including the semiconductor layer 21 and the semiconductor layer 22, a color filter CFir, and the micro lens ML are stacked.

A pixel separation layer STI is provided between each pair of the adjacent pixel areas on a surface side of the semiconductor layer 21 (a side in contact with the color filters). A pixel transistor 26 is provided between the semiconductor layer 21 and the wiring layer 23 at a position between each pair of the adjacent pixel areas. The pixel transistor 26 includes a source, a drain, and a channel region which are provided on a semiconductor layer 21 side, and includes a gate insulation film, a gate electrode, a source electrode, and a drain electrode which are provided on a wiring layer 23 side.

The wiring layer 23 includes an insulation layer 24, and wirings 25. An image signal Sci obtained by photoelectric conversion by the photodiodes is transmitted to the signal processing unit 12 via the pixel transistors 26 and the wirings 25.

In the first embodiment, a heart rate is detected from pulses in a bloodstream. Since a bloodstream flows through a blood vessel just below the skin, the intensity of a detection signal can be increased by use of an infrared band component with a long wavelength (a near infrared band component, for example) rather than use of a red band component in the visible light region.

Figure 3:
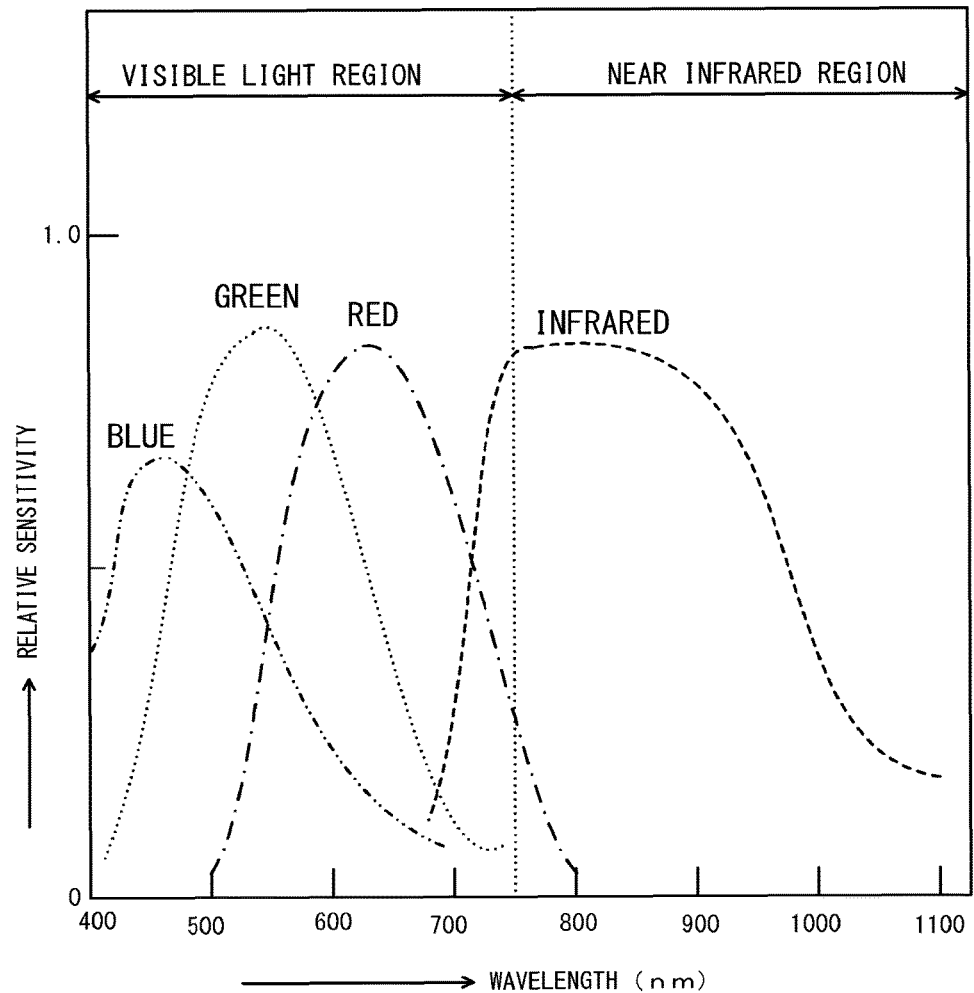
FIG. 3 is a diagram presenting relative sensitivities versus wavelength of color filters according to the first embodiment.

Characteristics of the color filters will be described with reference to FIG. 3. FIG. 3 is a diagram presenting relative sensitivities of the color filters versus wavelength.

As presented in FIG. 3, the color filter CFb is a visible band-pass filter having a maximum sensitivity at around a wavelength of 450 nm. The color filter CFg is a visible band-pass filter having a maximum sensitivity at around a wavelength of 530 nm. The color filter CFr is a visible band-pass filter having a maximum sensitivity at around a wavelength of 620 nm. The color filter CFir is a near infrared band-pass filter having a maximum sensitivity at around a wavelength of 750 to 850 nm. The infrared band-pass filter is made by using a perylene-based pigment, an azometan-based pigment, a bisbenzofuranone-based pigment, an epoxy-based pigment, an azo-based dye, a methacrylic resin, a glass filter, a photonic crystal, or the like.

In the first embodiment, the infrared band signal Sir is inputted to the image display unit 2, and an IR image at a night time can be obtained. In addition, since a blue band signal Sb, a green band signal Sg, and a red band signal Sr are also inputted at a night time, the resolution of the IR image can be made higher than that of a trichromatic (R (red), G (green), and B (blue)) image at a daytime.

A pixel array will be described with reference to FIG. 4. FIG. 4 is a schematic plan view illustrating a pixel array.

As illustrated in FIG. 4, the IR pixel is arranged at a rate of ¼. In FIG. 4, the IR pixel is arranged on the right upper side, the R pixel is arranged on the right lower side, the G pixel is arranged on the left lower side, and the B pixel is arranged on the left upper side.

Note that the pixel array may be modified as needed in consideration of a balance between the heart rate detection using infrared rays, and the quality of a captured color image. As illustrated in FIG. 5A, the IR pixel may be arranged at a rate of ¹⁄₁₆, for example, while the high sensitivity of heart rate detection is maintained. Instead, as illustrated in FIG. 5B, the IR pixel may be arranged at a rate of ¹⁄₆₄.

In the first embodiment, it is necessary to choose a material having a large light absorption coefficient in the visible light region and the infrared region (near infrared region, for example).

Figure 6:
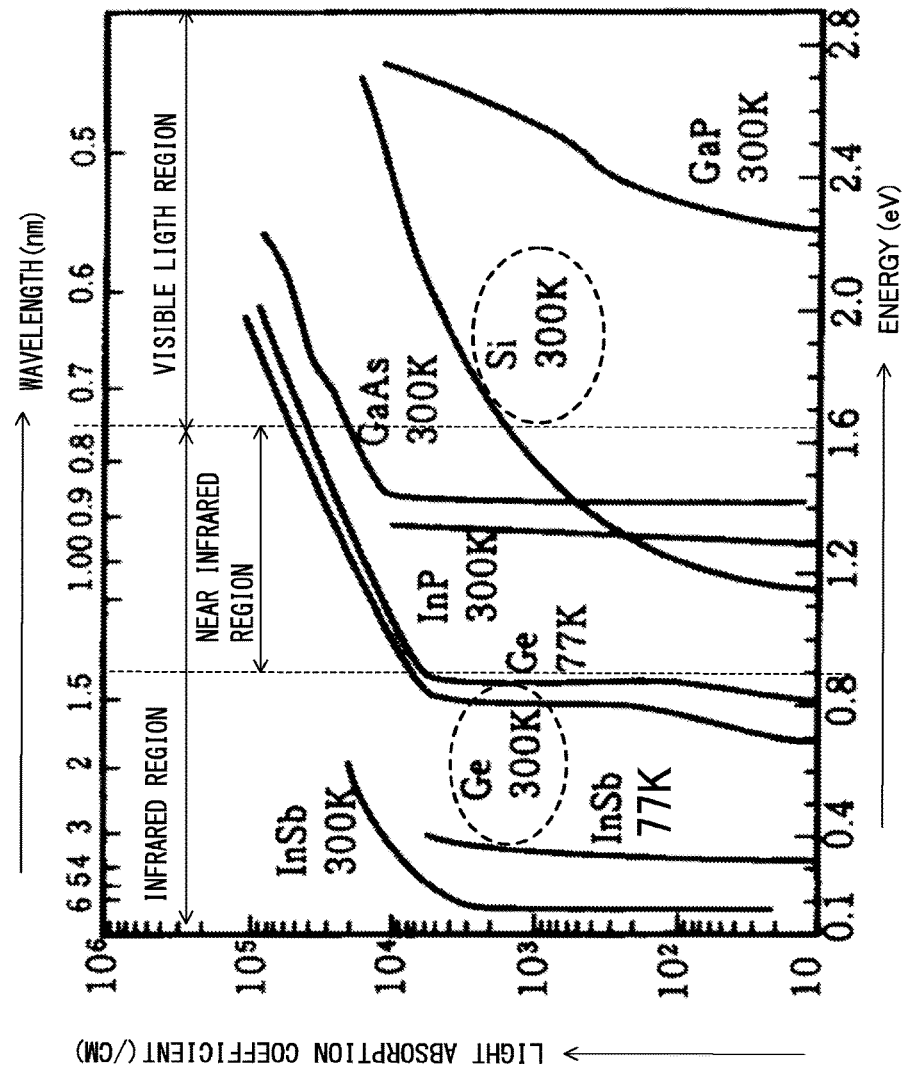
FIG. 6 is a characteristic chart presenting a light absorption coefficient of each material versus wavelength (energy)

Light absorption of a material forming a photodiode will be described with reference to FIG. 6. FIG. 6 is a characteristic chart presenting a light absorption coefficient versus wavelength (energy) of each material.

As presented in FIG. 6, the light absorption coefficient versus wavelength varies among materials. In comparison of silicon (Si) with germanium (Ge), for example, the silicon absorbs light of only about ¹⁄₃₀ of light absorbed by the germanium in the visible light region and the near infrared region. For this reason, the first embodiment uses silicon-germanium (SiGe) as a material for forming the image sensor 11 (constituent material for the semiconductor layer 21 and the semiconductor layer 22).

Here, since a silicon substrate is usually used as a material for forming an integrated circuit constituting the facial recognition system, silicon may also be used as a material for forming the image sensor 11. In this case, since the light reception sensitivity in the near infrared region is low, it is preferable to increase the IR pixel rate by re-designing the pixel array.

Alternatively, the image capture unit 1 may be formed of a one-ship integrated circuit using silicon-germanium as a material for the image sensor 11, and using a silicon substrate as a material for the signal processing unit 12.

The signal processing unit 12 receives the image signal Sci, and performs signal processing on the inputted image signal Sci. The signal processing unit 12 outputs a blue band signal Sb, a green band signal Sg, a red band signal Sr, and an infrared band signal Sir to the image display unit 2. The signal processing unit 12 outputs the infrared band signal Sir to the heart rate detection unit 4.

The image display unit 2 receives the blue band signal Sb, the green band signal Sg, the red band signal Sr, and the infrared band signal Sir. The image display unit 2 receives a transferred image data signal Stid from outside. The transferred image data signal Stid contains a photograph, a video image, or the like. The image display unit 2 receives an image data signal Sid and the like stored in the memory unit 6. The image data signal Sid contains any of various video images captured by the image capture unit 1. The image display unit 2 displays an image based on an inputted signal.

The facial recognition processing unit 3 receives an image information signal Sif outputted from the image display unit 2, and recognizes a face from the displayed image. A specific procedure of facial recognition will be described in detail later.

The heart rate detection unit 4 receives the infrared band signal Sir, the transferred image data signal Stid, and the image data signal Sid. The heart rate detection unit 4 reads the heart rate of a person from pulses in a bloodstream based on the inputted signals. Here, the heart rate detection unit 4 reads the heart rate of a person whose face is recognized by the facial recognition processing unit 3.

The authentication unit 5 receives a facial recognition signal Sfc outputted from the facial recognition processing unit 3, and receives a heart rate signal Shr outputted from the heart rate detection unit 4. The authentication unit 5 judges whether the person is the identical person or a photograph depending on the presence or absence of the heart rate.

Figure 7:
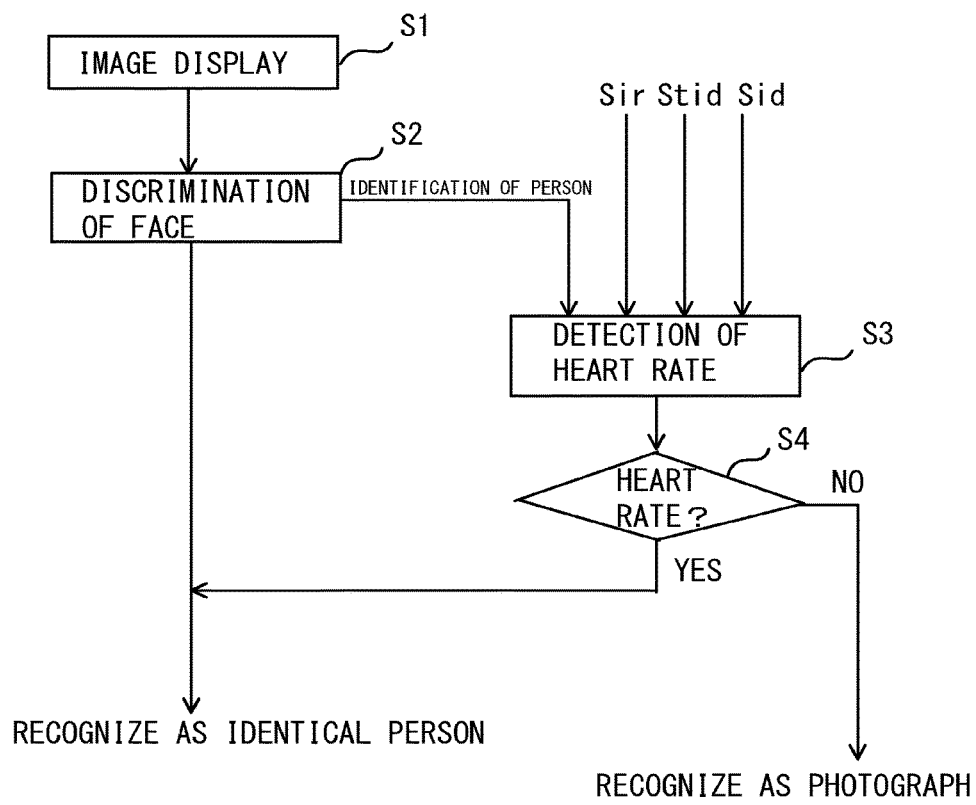
FIG. 7 is a diagram illustrating process steps of facial recognition according to the first embodiment.
Figure 8:
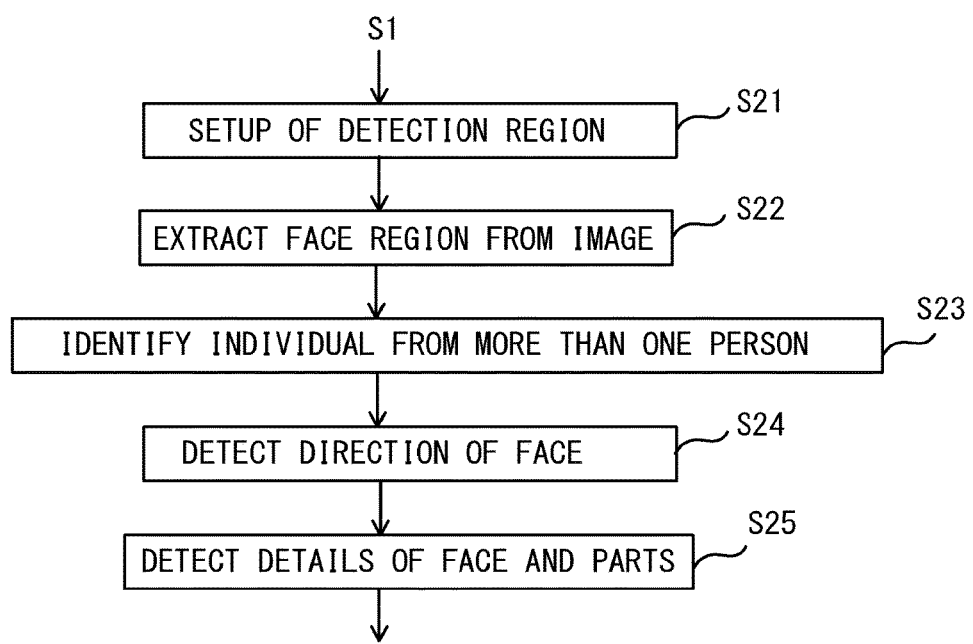
FIG. 8 is a diagram illustrating process steps of discrimination of a face according to the first embodiment.

Next, the face authentication using the facial recognition system will be described with reference to FIGS. 7 and 8. FIG. 7 is a diagram illustrating process steps of facial recognition. FIG. 8 is a diagram illustrating process steps of discrimination of a face.

As illustrated in FIG. 7, the image display unit 2 displays an image on a display screen (step S1). The facial recognition processing unit 3 discriminates the face of a particular person from a color image, for example, displayed on the display screen, the color image displaying more than one person, for example (step S2).

Details of the discrimination of a face will be described by use of FIG. 8. A detection region is set up in the display screen (step S21). A face region is extracted from the image in the set region (step S22). An individual is identified from more than one person (step S23). A direction of the face of the identified person is detected (step S24). Details of the face and parts are detected. Specifically, whether there is an obstacle that blocks transmission of infrared rays (such as a mask, glasses, or a muffler) is checked, and a face exposed region that is most suitable for bloodstream detection is determined (step S25).

The heart rate detection unit 4 receives the infrared band signal Sir, the image data signal Sid, and the transferred image data signal Stid. The heart rate detection unit 4 reads the heart rate of the person identified by the facial recognition processing unit 3 from pulses in a bloodstream based on a signal (signal in the infrared region) detected in the face exposed region of the person.

As described above, the heart rate detection device and the facial recognition system with the heart rate detection device in the first embodiment are each provided with the image display unit 2, the facial recognition processing unit 3, the authentication unit 5, the memory unit 6, and the heart rate detection device 80. The heart rate detection device 80 includes the image capture unit 1 and the heart rate detection unit 4. The image capture unit 1 includes the image sensor 11 and the signal processing unit 12. The image sensor 11 includes the B pixel (blue pixel), the G pixel (green pixel), the R pixel (red pixel), and the IR pixel (infrared pixel). The facial recognition processing unit 3 receives the image information signal Sif outputted from the image display unit 2, and recognizes the face from the displayed image. The heart rate detection unit 4 reads the heart rate of the person from the pulses in the bloodstream based on the inputted signal in the infrared region.

Thus, the heart rate can be detected with a high sensitivity. Therefore, the face authentication can be executed with a high accuracy by using the presence or absence of the heart rate.

In the first embodiment, the heart rate detection device 80 detects the heart rate of a human body, but what is detected is not necessarily limited to this. For example, the heart rate detection device 80 may be applied to detection of the heart rate of an animal such as a dog or cat.

Figure 9:
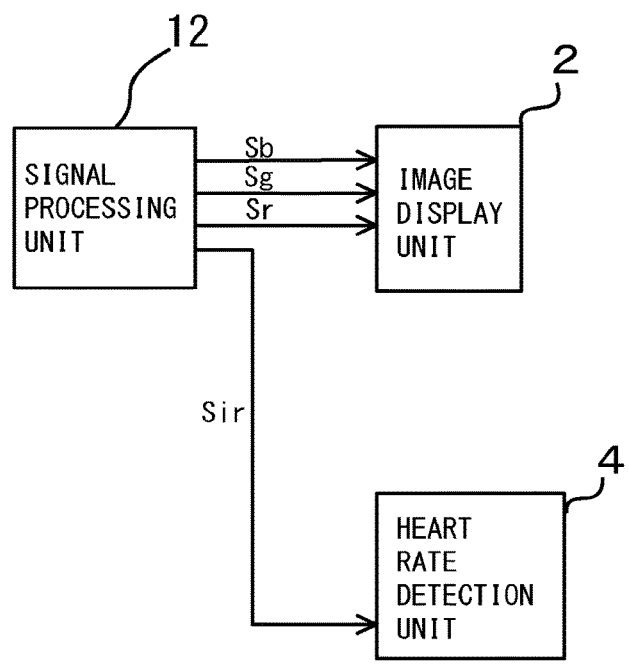
FIG. 9 is a diagram illustrating signals outputted from a signal processing unit in a daytime mode according to a second embodiment.
Figure 10:
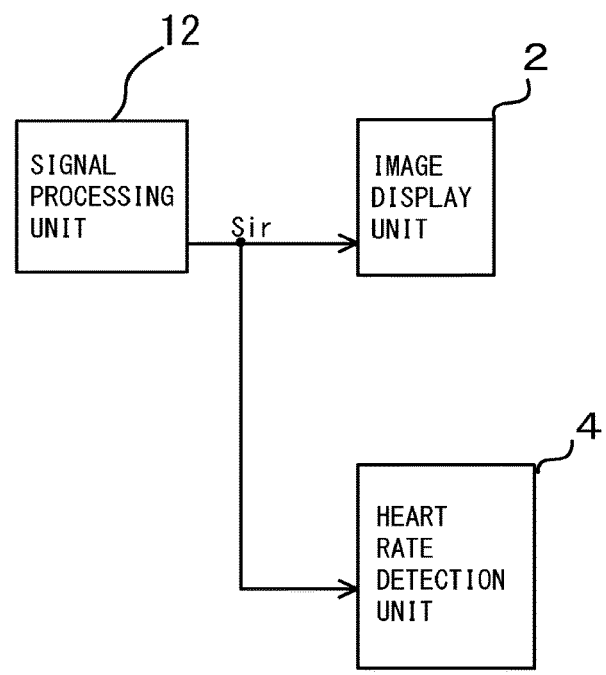
FIG. 10 is a diagram illustrating signals outputted from the signal processing unit in a night time mode according to the second embodiment.

A heart rate detection device and a facial recognition system with the heart rate detection device according to a second embodiment will be described with reference to the drawings. FIG. 9 is a diagram illustrating signals outputted from a signal processing unit in a daytime mode. FIG. 10 is a diagram illustrating a signal outputted from the signal processing unit in a night time mode. In the second embodiment, signals inputted to the image display unit differ between the daytime mode and the night time mode.

In the following description, the second embodiment will be described only for constituent portions different from those in the first embodiment, with the same constituent portions indicated by the same reference numerals and omitted from the description.

As illustrated in FIG. 9, in the facial recognition system in the second embodiment, the image display unit 2 in the daytime mode receives the blue band signal Sb, the green band signal Sg, and the red band signal Sr from the signal processing unit 12, and displays a color image on a video screen.

As illustrated in FIG. 10, in the facial recognition system in the second embodiment, the image display unit 2 in the night time mode receives the infrared band signal Sir from the signal processing unit 12, and displays an IR image on the video screen.

In the daytime mode, the facial recognition processing unit 3 receives a color image information signal Sif outputted from the image display unit 2, and recognizes the face from the displayed image. In the night time mode, the facial recognition processing unit 3 receives a monochrome image information signal Sif generated from the infrared band signal Sir outputted from the image display unit 2, and recognizes the face from the displayed image.

Here, a control unit (not illustrated) performs switching between the daytime mode and the night time mode automatically by time. Instead of this, the switching employed herein may be switching triggered by use of a "night view mode" which is one of automatic modes equipped in a camera, switching based on illumination determination or brightness determination, or switching with any other trigger.

The heart rate detection unit 4 receives the infrared band signal Sir. The heart rate detection unit 4 reads the heart rate of the person identified by the facial recognition processing unit 3 from pulses in a bloodstream based on a signal (signal in the infrared region) detected in the face exposed region of the person.

As described above, in the heart rate detection device and the facial recognition system with the heart rate detection device in the second embodiment, the signals inputted to the image display unit 2 differ between daytime and night time. At a night time, the facial recognition processing unit 3 receives a monochrome image information signal Sif generated from the infrared band signal Sir outputted from the image display unit 2, and recognizes the face from the displayed image. The heart rate detection unit 4 reads the heart rate of the person identified by the facial recognition processing unit 3 from pulses in a bloodstream based on a signal (signal in the infrared region) detected in the face exposed region of the person.

Thus, the heart rate can be detected with a high sensitivity. Therefore, the face authentication can be executed with a high accuracy by using the presence or absence of the heart rate.

While certain embodiments have been described, these embodiments have been presented by way of example only, and are not intended to limit the scope of the inventions. Indeed, the embodiments described herein may be embodied in a variety of the other forms; furthermore, various omissions, substitutions and changes in the form of the embodiments described herein may be without departing from the spirit of the inventions. The accompanying claims and their equivalents are intended to cover such forms or modifications as would fall within the scope and spirit of the inventions.

The invention claimed is:

1. A facial recognition system comprising:
   an image sensor including at least one blue pixel, at least one green pixel, at least one red pixel, and at least one infrared pixel, and configured to detect incident light by the at least one infrared pixel, and to output detected infrared information;
   circuitry configured to
      recognize the face of a person based on an image information signal captured by the image sensor and produce a facial recognition signal;
      read the heart rate of the person from pulses in a blood vessel in the face based on the infrared information;
      receive the facial recognition signal, authenticate the person as an identical person when the heart rate is inputted, and authenticate the person as a photograph when the heart rate is not inputted; and receive the image information signal outputted from the image sensor, and output a blue information signal, a green information signal, a red information signal, and an infrared information signal based on the image information signal; and an image display configured to perform image display and output the image information signal when the image display receives the blue information signal, the green information signal, the red information signal, and the infrared information signal, or receives an image data signal, wherein a proportion of a number of the at least one infrared pixel to a total number of pixels in the image sensor is smaller than at least one of a proportion of a number of the at least one blue pixel to the total number of pixels in the image sensor, a proportion of a number of the at least one green pixel to the total number of pixels in the image sensor, and a proportion of a number of the at least one red pixel to the total number of pixels in the image sensor, and a quality of a captured color image in the image information signal is determined by the proportion of the number of the at least one infrared pixel to the total number of pixels in the image sensor.

2. The facial recognition system according to claim 1, wherein the image data signal is image information stored in a memory unit or image information transferred from outside.

3. The facial recognition system according to claim 1, wherein the at least one infrared pixel is arranged at a rate of 1/16 or 1/64 in a pixel array including the at least one infrared pixel, the at least one blue pixel, the at least one green pixel, and the at least one red pixel.

4. The facial recognition system according to claim 1, wherein the circuitry is configured, in a daytime mode, to output the blue information signal, the green information signal, and the red information signal to the image display unit, and to use the infrared information signal to read the heart rate, and the circuitry is configured, in a night time mode, to output the infrared information signal to the image display, and to use the infrared information signal to read the the heart rate.

5. The facial recognition system according to claim 4, wherein switching between the daytime mode and the night time mode is performed by employing any one of automatic switching by time, switching triggered by a night view mode of a camera, and switching based on illumination determination or brightness determination.

6. The facial recognition system according to claim 1, wherein the at least one infrared pixel includes a SiGe photodiode to capture the incident light via an infrared band-pass filter.

7. The facial recognition system according to claim 6, wherein the infrared band-pass filter is made by using a methacrylic resin, an azo-based dye, a perylene-based pigment, an azometan-based pigment, a bisbenzofuranone-based pigment, an epoxy-based pigment, a glass filter, or a photonic crystal.

8. The facial recognition system according to claim 1, wherein the facial recognition system is equipped in a handheld terminal.

* * * * *